(12) United States Patent
Pospisil et al.

(10) Patent No.: US 6,709,268 B2
(45) Date of Patent: Mar. 23, 2004

(54) ORTHODONTIC APPLIANCE WITH CONTOURED RETAINING GUIDE

(75) Inventors: Jirina V. Pospisil, Hacienda Heights, CA (US); David E. Solid, Monrovia, CA (US); Oliver L. Puttler, La Crescenta, CA (US); John A. Verdouw, Ontario (CA)

(73) Assignee: 3M Innovative Properties Company, St. Paul, MN (US)

( * ) Notice: Subject to any disclaimer, the term of this patent is extended or adjusted under 35 U.S.C. 154(b) by 60 days.

(21) Appl. No.: 10/017,326

(22) Filed: Dec. 14, 2001

(65) Prior Publication Data

US 2003/0113682 A1 Jun. 19, 2003

(51) Int. Cl.$^7$ ................................ A61C 7/00
(52) U.S. Cl. ............................ 433/17; 433/10
(58) Field of Search ................... 33/8, 9, 10, 11, 33/13, 17

(56) References Cited

U.S. PATENT DOCUMENTS

| | | | |
|---|---|---|---|
| 3,758,947 A | | 9/1973 | Kesling |
| 4,820,151 A | | 4/1989 | Pospisil |
| 4,878,840 A | * | 11/1989 | Reynolds ................ 433/9 |
| D306,207 S | | 2/1990 | Hannan et al. |
| 4,927,360 A | | 5/1990 | Pospisil |
| 4,963,092 A | | 10/1990 | Snead |
| 5,095,602 A | | 3/1992 | Reher et al. |
| 5,380,196 A | * | 1/1995 | Kelly et al. .............. 433/8 |
| 6,042,374 A | * | 3/2000 | Farzin-Nia et al. ...... 433/13 |
| 2001/0029008 A1 | | 10/2001 | Jordan et al. |

FOREIGN PATENT DOCUMENTS

EP  0 820 735  1/1998

OTHER PUBLICATIONS

3M Unitek Product Catalog 2001–2002, pp. 3–1 to 3–17.
GAC Orthodontic Catalog Copyright 1997, pp. 58–77.
GAC Orthodontic Products, (1983), pp. A1, E1–E10.
U.S. Ser. No. 09/848,030 filed May 3, 2001.
U.S. Ser. No. 10/017,531, filed Dec. 14, 2001.

* cited by examiner

*Primary Examiner*—Kevin Shaver
*Assistant Examiner*—Melba Bumgarner
(74) *Attorney, Agent, or Firm*—James D. Christoff

(57) ABSTRACT

An appliance used in orthodontic treatment includes a retaining guide that extends outwardly in an occlusal and/or a gingival direction. The retaining guide presents a smoothly contoured, domed shape having a relatively low profile for avoiding contact with opposing dentition or orthodontic appliances that are connected to opposing dentition. The retaining guide is useful for keeping a wire segment or other item in place and in contact with a body of the appliance so that the item does not detach from the appliance during the course of treatment. The retaining guide is particularly useful for keeping tieback loops and other items made from wire segments in place.

24 Claims, 2 Drawing Sheets

ORTHODONTIC APPLIANCE WITH CONTOURED RETAINING GUIDE

BACKGROUND OF THE INVENTION

1. Field of the Invention

This invention relates to an appliance that is fixed to a patient's tooth during the course of orthodontic treatment. The appliance has a small retaining guide to hold a wire segment or another item connected to the appliance in place.

2. Description of the Related Art

Orthodontic treatment involves movement of malpositioned teeth to desired locations along the dental arches. Orthodontic treatment provides improved occlusion so that the teeth function better together during chewing. Orthodontic treatment can also greatly enhance the aesthetic appearance of the patient's oral cavity by realigning crooked teeth and eliminating gaps or spaces between adjacent teeth.

One common form of orthodontic treatment is carried out by the use of tiny, slotted appliances known as brackets that are secured to the patient's anterior, cuspid and bicuspid teeth. An archwire is received in the slot of the appliances and forms a track to guide movement of the teeth to desired positions. Ends of the archwires are often received in passageways of small appliances known as buccal tubes that are secured to the patient's molar teeth.

Many orthodontic appliances have small, curved protrusions known as tiewings that extend outwardly from a central body of the appliance. For example, certain brackets have two spaced apart tiewings that extend in a gingival direction (i.e., a direction toward the patient's gingiva or gums). Those brackets also often have two spaced apart tiewings that extend in an occlusal direction (i.e., in a direction toward the outer tips of the patient's teeth). The gingival tiewings are connected to a central body of the bracket along a gingival side of the archwire slot and the occlusal tiewings are connected to the bracket body along an occlusal side of the archwire slot.

Tiewings are commonly used by the orthodontist during treatment to hold the archwire in the archwire slot. To this end, a ligature is placed along the back or lingual side of the occlusal tiewings and the gingival tiewings and is also placed over the front or labial side of the archwire. (As used herein, the word "lingual" refers to a direction toward the patient's tongue, while the word "labial" refers to a direction toward the patient's lips or cheeks.) In many instances, the ligature holds the archwire in contact with the bottom or lingual side of the archwire slot. However, in instances where the tooth is significantly maloccluded and initially located some distance from the archwire, the ligature serves to urge the archwire in a direction toward the bottom of the archwire slot.

In general, there are two types of ligatures in widespread use. One type of ligature is in the form of a tiny elastomeric O-ring. The O-ring is sufficiently flexible such that it can be stretched around and behind the tiewings as well as over the front side of the archwire. Once the O-ring is in place, the inherent memory of the elastomeric material tends to return the O-ring toward its normally compact, unstretched configuration. This contracting force urges the archwire toward the bottom of the archwire slot and also helps to retain the ligature in place.

Other types of ligatures are known as wire ties. These ligatures are made from short lengths of wire such as stainless steel wire having a small cross-sectional diameter.

In use, the orthodontic practitioner extends the wire ligature around the backs of the tiewings as well as across the front side of the archwire, and then twists the free ends of the ligature together. Once the ends are twisted together and any slack in the ligature has been removed, the archwire is retained in the archwire slot or is urged toward the same.

The tiewings of the orthodontic appliances described above typically have a concavity in the form of a curved groove or notch that extends along the lingual side of the tiewing. For example, many tiewings have a semi-cylindrical lingual concavity that is oriented such that the central axis of the semi-cylindrical shape is approximately parallel to the longitudinal axis of the archwire slot. In some instances, the opposite side (or labial side) of the tiewing is generally flat and co-planar with a labial side of the appliance body. In other instances, the labial side of the tiewing has a curved configuration complemental to the curved concavity of the lingual side, such that the tiewing has an overall, somewhat hook-shaped or "C"-shaped configuration.

The lingual concavity of the tiewings as described above is generally considered important since it helps to retain the ligature in place during the course of treatment. Ligatures that become detached from appliances in use represent a significant nuisance since they may be inadvertently swallowed by the patient. In addition, appliances that are no longer connected to archwires due to missing ligatures are ineffective in moving the associated tooth, and as a result the length of treatment time may be extended.

As a consequence, manufacturers of orthodontic appliances have often designed and constructed tiewings to reduce the likelihood that the ligature will become detached from the appliance during the course of treatment. To this end, the lingual concavity of the tiewings typically is sufficiently large to extend around a substantial portion (such as one-half) of the periphery of the ligature when considered in cross-sectional reference planes. Ligatures that are deeply seated in the concavity during use are less likely to slip off of the tiewing and become disengaged from the appliance.

However, ligatures are available in a wide variety of cross-sectional sizes and shapes. Wire ligatures typically have a round cross-sectional shape with diameters ranging from about 0.008 in. (0.20 mm) to about 0.014 in. (0.36 mm). Ligatures made from an elastomeric material often have a cross-sectional diameter that is much larger, such as about 0.030 in. (0.76 mm) when relaxed and about 0.020 in. (0.5 mm) when in use. Furthermore, elastomeric ligatures are also known having cross-sectional shapes other than circular (see, e.g., U.S. Pat. No. 3,758,947).

As a result, the tiewings of orthodontic appliances are often provided with relatively large lingual concavities in order to accommodate any one of the wide variety of ligature sizes that might be selected by the orthodontic practitioner. This large lingual concavity tends to increase the overall size of the tiewing. Furthermore, tiewings are also designed with relatively thick cross-sections so that they are less likely to fracture and break off from the body of the appliance during use. Strong tiewings are deemed important because the tiewings are sometimes subjected to large forces, such as when a tiewing encounters a relatively hard food object in the oral cavity while the patient is eating.

Consequently, the tiewings of orthodontic appliances are often bulky in relation to remaining structural aspects of the appliance. The relatively large size of the tiewings is considered a disadvantage, however, because it increases the likelihood of contact with opposing dentition or with appliances mounted on opposing dentition. Tiewings may also contact adjacent soft tissue in the oral cavity and cause an irritation.

Manufacturers of orthodontic appliances have sometimes omitted tiewings when designing buccal tubes. The archwire passageways of buccal tubes are often closed along four sides, in contrast to the archwire passageways or slots of orthodontic brackets that are open along one side. When the ends of the archwires are inserted in the closed passageways, ligatures for connecting the archwire to the buccal tube appliance are not needed. The elimination of tiewings from such appliances helps to ensure that the appliance does not unduly bear against other structure in the oral cavity.

However, there are some instances where orthodontic practitioners prefer to use a buccal tube appliance having tiewings. For example, some buccal tubes for first molar teeth have a passageway that can be opened along one side for converting the buccal tube to a bracket. Opening of the passageway is often carried out in adolescent patients after that patient's adjacent second molar tooth has erupted sufficiently to receive a buccal tube on its surface. Once the passageway of the buccal tube on the first molar tooth has been opened, the tiewings serve to hold a ligature in place.

Additionally, there may be a gap between adjacent teeth at one or more locations along the dental arch. In those instances, the practitioner may elect to install a wire segment known as a "tieback loop" to move teeth along the length of the arch and close the gap. Typically, one side of the tieback loop is connected to a buccal tube, while the opposite side of the loop is connected to an appliance that is located on the opposite side of the gap.

Some practitioners prefer to connect tieback loops to a hook of the buccal tube appliance. However, other practitioners prefer to connect tieback loops to the body of the buccal tube appliance. In those instances, the loop extends along the occlusal, distal and gingival sides of the buccal tube body in a location next to the base. Once the ends of the tieback loop are twisted together to remove slack, the tiewings help ensure that the loop does not slip off the body. Unfortunately, the tiewings are often considered troublesome for the reasons mentioned above.

In the past, a rear portion of some buccal tube appliances extends in a distal direction (i.e., in a direction away from the center of the patient's dental arch) in spaced, overhanging relation to the base. This overhanging portion presents a notch adjacent the base of the appliance which can be used to receive a tieback loop. However, the notch is often considered unsatisfactory, since the tieback loop when received in the notch interferes with an archwire extending through the archwire passageway.

At present, there is a need in the art for an orthodontic appliance having improved features for securely retaining tieback loops and other items in place as needed. Preferably, such an appliance has an overall relatively compact configuration to reduce the likelihood that it might contact the opposing teeth of the other dental arch, bear against orthodontic appliances that are mounted on the opposing teeth or irritate adjacent soft tissue.

SUMMARY OF THE INVENTION

The present invention is directed to an orthodontic appliance with a contoured retaining guide that presents a low profile. The retaining guide functions to keep a wire segment or other item in place during the course of treatment. Preferably, the retaining guide is smoothly curved and lacks any substantial recess or concavity that might otherwise trap food particles and other debris.

The retaining guide of the present invention is particularly useful for keeping a tieback loop in a proper orientation on the appliance and in a securely coupled relationship to the appliance. Examples of suitable appliances include buccal tube appliances, bracket appliances and self-ligating appliances, including appliances that lack tiewings as well as appliances that have tiewings. Preferably, the retaining guide has an outer domed surface that slopes gradually from adjacent surfaces of the appliance body. The guide also preferably has a gently rounded, low profile outer edge that reduces the likelihood of interference with other structure in the oral cavity.

In more detail, the present invention is directed in one aspect to an orthodontic appliance that comprises a base and a body extending outwardly from the base. The body has an occlusal side, labial side and a gingival side. The body also has a mesial end and a distal end. The appliance further includes an elongated archwire passageway for receiving an archwire, and a guide extending away from the body for retaining a wire segment or other item in place. The guide is connected to one of the occlusal side and the gingival side of the body. The guide has an overall dome-shaped configuration when viewed in a direction toward the base.

Another aspect of the present invention is also directed toward an orthodontic appliance that comprises a base and a body extending from the base. The body has an occlusal side, a labial side and a gingival side. The appliance also includes an elongated archwire passageway for receiving an archwire, and a guide extending away from the body. The guide is connected to one of the occlusal side and the gingival side of the body. The guide has an outer edge section remote from the body and extends in a mesial-distal direction a certain distance. This certain distance increases in size as the outer edge section is approached.

A further aspect of the present invention also directed toward an orthodontic appliance. The appliance according to this aspect has a base and a body extending outwardly from the base. The body has an occlusal side, a labial side and a gingival side. The appliance also includes an elongated archway passageway for receiving an archwire, and a guide extending away from the body for retaining a wire segment or other item in place. The guide is connected to one of the occlusal side and the gingival side of the body and has an outer edge section remote from such side. The outer edge section when viewed in a lingual direction extends along a path that does not exceed an angle of 45 degrees with respect to the certain side.

An additional aspect of the invention is also directed to an orthodontic appliance that has a base and a body extending outwardly from the base. The body has an occlusal side, a labial side and a gingival side. The appliance additionally includes an elongated archwire passageway for receiving an archwire. A retaining guide extends away from the body and is connected to one of the occlusal side and the gingival side of the body. The guide has an overall generally triangular configuration when viewed in a direction toward the body along a generally occlusal-gingival reference axis.

These and other aspects of the invention are described in more detail below and are illustrated in the accompanying drawings.

DETAILED DESCRIPTION OF THE PREFERRED EMBODIMENTS

Figure 1:
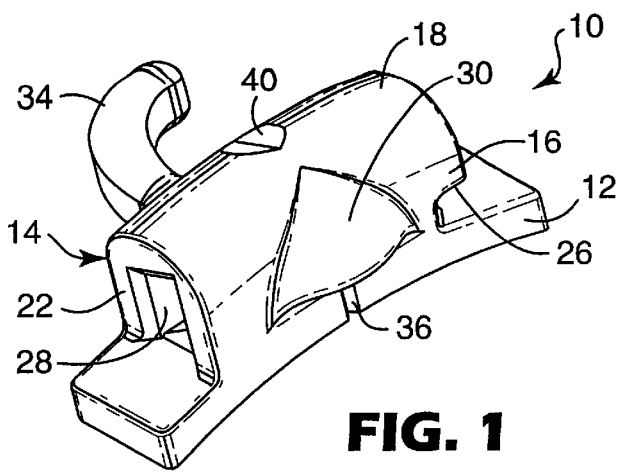
FIG. 1 is a perspective view of an orthodontic appliance according to one embodiment of the invention, looking at the appliance toward its occlusal, mesial and labial sides.

An orthodontic appliance according to one embodiment of the invention is illustrated in FIGS. 1–4 and is broadly designated by the numeral 10. The appliance 10 includes a base 12 for attachment by welding or brazing to a band that extends around a patient's tooth. The band helps ensure that the appliance 10 does not become detached from the tooth during the course of treatment.

As an alternative, the base 12 may have an exterior, lingually-facing surface that is adapted for direct bonding to the patient's tooth. In that instance, the surface is preferably provided with one or more types of mechanical and/or chemical retention-enhancing means to help ensure that the appliance 10 remains securely bonded to the tooth during the course of treatment. Suitable mechanical and chemical retention means are well known in the art and include, for example, grooves, particles, recesses, undercuts, spheres and adhesion-promoting agents. Preferably, the base 12 has a compound concave contour that is adapted to match the compound convex contour of the patient's tooth surface.

The appliance 10 also includes a body 14 that extends outwardly from the base 12. The body 14 includes an occlusal side 16, a labial side 18 and a gingival side 20. As can be best appreciated by reference to FIGS. 1 and 4, the occlusal, labial and gingival sides 16, 18, 20 together present a smoothly rounded overall shape when considered in mesial or distal view, although other configurations are also possible.

Figure 2:
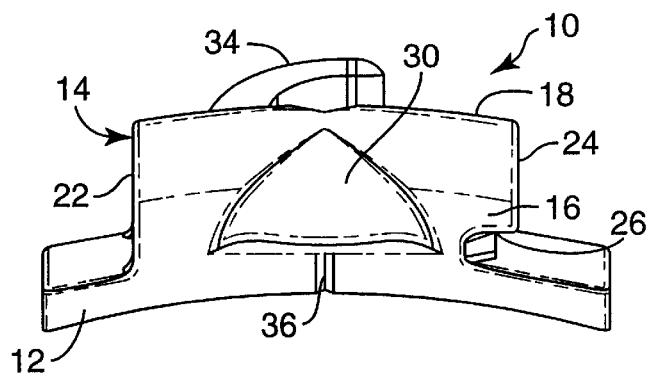
FIG. 2 is an elevational view of the appliance depicted in FIG. 1, looking at the appliance toward its occlusal side.
Figure 3:
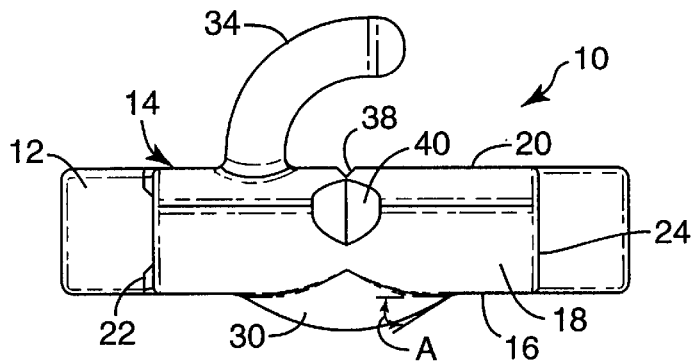
FIG. 3 is a elevational view of the appliance shown in FIGS. 1 and 2, looking at the appliance toward its labial side.
Figure 4:
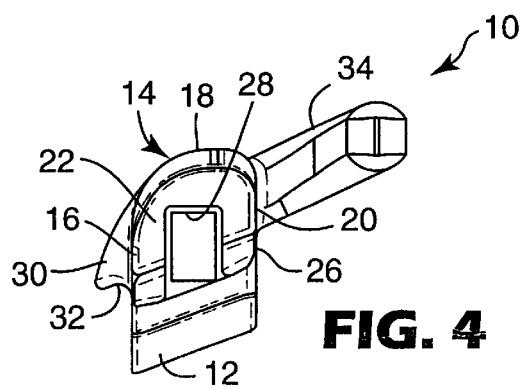
FIG. 4 is an elevational view of the appliance shown in FIGS. 1–3, looking at the appliance toward its distal end.

The body 14 also includes a mesial end 22 and a distal end 24 that is remote from the mesial end 22. The distal end 24 includes a notch or groove 26 that is shown in FIGS. 1, 2 and 4. The groove 26 is next to the base 12 and extends from the occlusal side 16 to the gingival side 20 of the body 14.

The appliance 10 also has an elongated archwire passageway 28 that extends from the mesial end 22 to the distal end 24 of the body 14. The passageway 28 in this embodiment has a generally rectangular shape in transverse cross-sectional view as shown in FIG. 4, although other shapes are also possible. The passageway 28 has an overall size that is adapted to complementally receive an archwire having a similar rectangular configuration in transverse cross-sectional view.

The appliance 10 additionally has a retaining guide 30 having a low profile, contoured shape. The retaining guide 30 in this embodiment is connected to the occlusal side 16 of the body 14, although other locations are also possible.

For example, the retaining guide 30 may alternatively be connected to the gingival side 20 of the body 14.

The guide 30 has an overall dome-shaped configuration when viewed toward a lingual direction or in a direction toward the base 12 of the appliance 10. This dome-shaped configuration can be seen, for example, in FIG. 3. As shown, the shape of the dome is relatively low and does not extend a significant distance from the occlusal side 16 in an occlusal direction. Preferably, the outer occlusal curved edge of the guide 30 extends along a path that is no more than about 0.020 in. (0.5 mm) from the occlusal side 16 of the body 14. As shown for example in FIGS. 1–3, the outer occlusal curved edge of the guide 30 intersects the occlusal side 16.

Moreover, the slope of the domed-shaped configuration is preferably relatively shallow. For example, and referring to FIG. 3, a straight line drawn tangent to the steepest portion of the outer edge of the guide 30 is preferably no more than 45 degrees, and more preferably no more than 30 degrees from a reference line extending longitudinally across the occlusal side 16. This angle is designated "A" in FIG. 3 and generally lies in a reference plane that is perpendicular to the labial-lingual axis of the appliance 10.

The retaining guide 30 also preferably has an overall, generally triangular configuration when viewed in a gingival direction toward the body 14, as can be appreciated by reference to FIG. 2. This overall generally triangular configuration is oriented such that the apex of the triangle is pointing in a labial direction and the base of the triangle is facing a lingual direction and is located next to the base 12. As a result, the width of the guide 30 in a mesial-distal direction increases in size as the outer edge (i.e., the curved lingual-occlusal edge) of the guide 30 is approached.

The retaining guide 30 has a lingual side 32 (FIG. 4) for contact with a ligature. Optionally, the lingual side 32 extends in a curve about a reference axis that is generally parallel to the longitudinal axis of the archwire passageway 28.

The appliance 10 also includes a hook 34 for optional connection to another orthodontic device. Examples of suitable devices include coil springs and elastomeric force modules that are connected to other appliances in the patient's oral cavity. Optionally, such devices have an end section with a hole or opening that receives the hook 34, although other types of connections are also possible.

The hook 34 in this embodiment has an overall curved configuration that extends from the gingival side 20 of the body 14. The curved longitudinal axis of the hook 30 extends away from the body 14 first in a gingival direction, and then in a distal direction. Preferably, all of the surfaces of the hook 34 are smoothly rounded to avoid irritating soft tissue in the oral cavity.

Optionally, the appliance 10 includes one or more positioning notches to help align the appliance 10 to the patient's tooth or to a band in instances where the appliance 10 is assembled to a band. In the embodiment shown in the drawings, the appliance 10 includes a small occlusal groove 36 (FIGS. 1 and 2) adjacent the guide 30 and a gingival groove 38 (FIG. 3) that is adjacent the hook 34. The appliance 10 preferably also includes a labial groove or notch 40 that is adapted to receive the end of a positioning tool, so that the practitioner can more easily exert a force on the appliance 10 as may be needed to precisely shift it to a desired location on the tooth structure.

Figure 5:
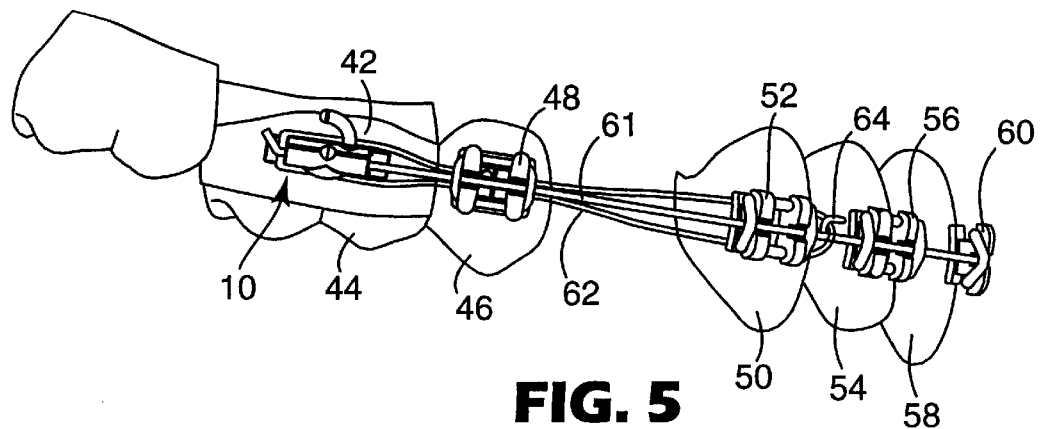
FIG. 5 is a reduced elevational view showing for exemplary purposes the appliance of FIGS. 1–4 as it might appear when mounted on an upper first molar tooth of a patient undergoing orthodontic treatment, and also showing a set of additional appliances mounted on other teeth, an archwire connected to the appliances and a tieback loop used to close a space between two adjacent teeth of the patient.

FIG. 5 illustrates an example of use of the appliance 10 for a patient undergoing orthodontic therapy. In this example, the appliance 10 is secured to an orthodontic metallic band 42 by welding, brazing or other means. In turn, the band 42 is placed over the patient's first upper right molar tooth 44. Preferably, a luting cement is spread along the inside of the band 42 before the band 42 is placed on the tooth 44 in order to fill any gaps or voids and to strengthen the connection between the band 42 and the tooth 44.

The remaining teeth in FIG. 5 each receive an orthodontic bracket. In particular, a bicuspid tooth 46 receives a bracket 48, a cuspid tooth 50 receives a bracket 52, a lateral tooth 54 receives a bracket 56 and a central tooth 58 receives a bracket 60. For exemplary purposes, the illustrated brackets 48, 52, 56, 60 are metallic brackets that are directly bonded to the patient's tooth enamel, although other brackets and/or methods of connection could be utilized.

An archwire 61 is connected to the slots of the brackets 48, 52, 56, 60 and is inserted in the passageway 28 of the appliance 10. In this example, the patient has a gap between the bicuspid tooth 46 and the cuspid tooth 50. During orthodontic treatment, it is often desired to close such spaces for aesthetic purposes. Moreover, if the space is not closed, the teeth may drift over a period of time and assume new positions that arecrooked or otherwise unsatisfactory.

Consequently, the orthodontic practitioner faced with the scenario presented in FIG. 5 may elect to use a tieback loop to move the teeth together and close the gap. The tieback loop in FIG. 5 comprises a wire segment 62 that interconnects the appliance 10, the bicuspid bracket 48 and the cuspid bracket 52. An example of a suitable wire segment 62 is stainless steel wire having a diameter in the range of about 0.010 in. (0.25 mm) to about 0.014 in. (0.35 mm).

The wire segment 62 is installed along a path that extends along the gingival and occlusal sides of the brackets 48, 52 and the gingival side 20, the distal end 24 and the occlusal side 16 of the appliance 10. In particular, the wire segment 62 is placed against the lingual side 32 of the retaining guide 30 of the appliance 10, within the distal groove 26 and also along the lingual side of the hook 34. The wire segment 62 is also placed behind (i.e., on a lingual side of) the tiewings of the bicuspid bracket 48 and the cuspid bracket 52.

In this example, an auxiliary hook 64 has been secured to the archwire 61 in a location between the cuspid bracket 52 and the lateral bracket 56. The auxiliary hook 64 is secured to the archwire 61 by a spot welding operation, although other types of connections (such as cinch-type connections) are also possible. The ends of the wire segment 62 are then twisted together in a location adjacent the hook 64 in order to remove excess slack in the installed wire segment 62 and tightly secure the assembly together.

The present invention is an advantage, in that the forces exerted (or resisted) by the wire segment 62 lie along a path that is essentially collinear with the curved longitudinal axis of the archwire 61. As such, undesirable rotation or other movements of the teeth 44, 46, 50 may be avoided. Moreover, the wire segment 62 when arranged as shown in FIG. 5 forms a relatively compact assembly with the appliance 10 and the associated brackets 48, 52.

By way of comparison, it is possible for the distal end of the wire segment 62 to extend around the hook 34 of the appliance 10 instead of in a path along the occlusal side 16, the distal groove 26 and the gingival side 20 of the appliance 10. However, the resultant force exerted or resisted by the wire segment 62 in that instance is not as aligned with the longitudinal axis of the archwire 61 as it is in the arrangement depicted in FIG. 5. As a consequence, one or more of the teeth 44, 46, 50 may tilt or pivot in one or more directions to an undesirable new orientation.

Figure 6:
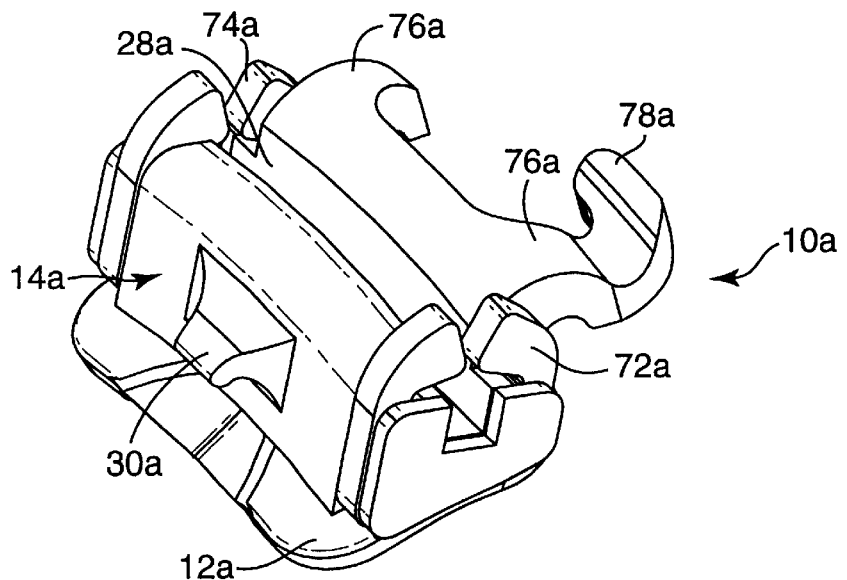
FIG. 6 is a perspective view of an orthodontic appliance according to another embodiment of the invention, looking at the appliance toward its occlusal, labial and mesial sides.
Figure 7:
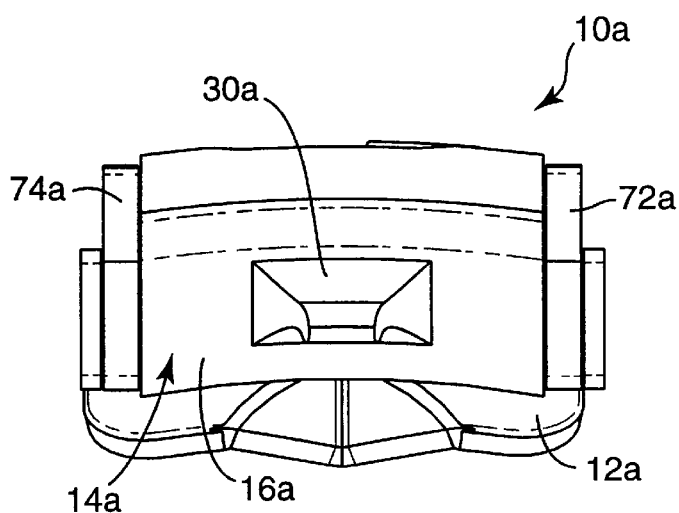
FIG. 7 is an elevational view of the appliance shown in FIG. 6, looking at the appliance toward its occlusal side.

An orthodontic appliance 10a according to another embodiment of the invention is illustrated in FIGS. 6 and 7. The appliance 10a includes a base 12a and a body 14a that extends outwardly from the base 12a. The body includes an occlusal side 16a and a gingival side (not shown). An elongated archwire passageway 28a extends in a generally mesial-distal direction across the body 14a.

The appliance 10a is of a type known as a "self-ligating" bracket. To this end, the appliance 10a has a latch that comprises a mesial spring clip 72a and a distal spring clip 74a. When an orthodontic archwire (not shown) is urged in a direction toward the bottom of the archwire passageway 28a, the clips 72a, 74a deflect and spread open to enable the archwire to be moved fully into the passageway 28a. Once the archwire is seated in the passageway 28a, the inherent resiliency of the clips 72a, 74a causes the same to shift to their relaxed, closed position as depicted in FIGS. 6 and 7 for retaining the archwire in the passageway 28a.

Preferably, the sides of the clips 72a, 74a deflect outwardly to a slot-open orientation and release the archwire from the archwire passageway 28a whenever the force exerted by the archwire on the appliance 10a exceeds a certain minimum value. The minimum value is sufficiently high to prevent the archwire from unintentionally releasing from the archwire passageway 28a during the normal course of orthodontic treatment. As such, the archwire can exert forces on the appliance 10a sufficient to carry out the intended treatment program and move the associated tooth as desired. Preferably, the clips 72a, 74a release the archwire from the archwire passageway 28a in a direction perpendicular and away from the lingual side of the archwire passageway 28a whenever the archwire exerts a force in the same direction on the appliance 10a that is in the range of about 0.2 lb (0.1 kg) to about 11 lbs (5 kg), more preferably in the range of about 0.4 lb (0.2 kg) to about 5.5 lbs (2.5 kg), and most preferably in the range of about 0.4 lb (0.2 kg) to about 2.7 lbs (1.25 kg).

To determine the force to release the archwire from the clips 72a, 74a, an elongated section of archwire is selected having an area in longitudinally transverse section that is complemental to (i.e., substantially fills) the cross-sectional area of the archwire passageway 28a. Next, a sling is constructed and is connected to the archwire section in two spaced apart locations that are closely adjacent but not in contact with the mesial and distal ends of the appliance 10a. Optionally, the sling is welded or brazed to the archwire section. Next, the sling is pulled away from the appliance 10a while the appliance 10a is held in a stationary position, taking care to ensure that the longitudinal axis of the archwire section does not tip relative to the longitudinal axis of the archwire passageway 28a. The force to release the archwire from the clips 72a, 74a is determined by use of an Instron testing apparatus connected to the sling, using a crosshead speed of 0.5 in/min (1.3 cm/min).

Preferably, the minimum value for self-release (i.e., self-opening) of the clips 72a, 74a is together substantially less than the force required in the same direction to debond the appliance 10a from the associated tooth in instances where the appliance 10a is directly bonded to the tooth surface. The minimum value for self-release of the clips 72a, 74a is preferably less than about one-half of the force required in the same direction to debond the appliance 10a from the associated tooth. For example, if the expected bond strength of the adhesive bond between the appliance 10a and the associated tooth is 16 lbs (7.3 kg) in a buccolabial direction, the clips 72a, 74a are constructed to self-release the archwire whenever the archwire exerts a force in the same buccolabial direction on the appliance 72a, 74a that is somewhat greater than about 8 lbs (3.6 kg).

The self-releasing clips 72a, 74a are a benefit to the practitioner, in that the likelihood of spontaneous debonding of the appliance 10a is substantially reduced. For example, if the practitioner attempts to place a relatively large archwire in the archwire passageway 28a and the clips 72a, 74a open and self-release the archwire as soon as the practitioner releases the archwire, the practitioner can then use an archwire with less stiffness in its place. As another example, if the archwire is initially held in the passageway 28a by the clips 72a, 74a and the archwire subsequently exerts a larger force on the appliance 10a (as may occur, for example, when the archwire encounters a hard object such as when the patient is chewing relatively hard food), the clips 72a, 74a will deflect to their slot-open orientations to release the archwires so that the appliance 10a does not debond from the tooth. Treatment can then be resumed by merely replacing the archwire in the archwire passageway 28a without the need to rebond the base 12a of the appliance 10a to the associated tooth.

Each clip 72a, 74a is preferably made from a flat annealed superelastic material having a pickled surface. Preferably, the superelastic material is nitinol having a nickel content of 55.97% by weight and an $A_f$ of 10°±5° C. The nitinol is cold worked to 37.5% and has a thickness in the range of about 0.012 in. (0.3 mm) to about 0.016 in. (0.4 mm). The clips 72a, 74a are first cut in a rough cutting EDM process, and then cut along their edges for an additional one or more times using an EDM process in order to smooth the edges. As another option, the clips 72a, 74a are cut from a section of tubing that is made from a shape memory alloy. Suitable shape memory alloys include alloys of nitinol and beta-titanium. The tubing is cut with a slot to form the opposed arm portions that are shown in FIGS. 6 and 7.

Other details and features of the latch and the clips 72a, 74a are set out in applicant's co-pending U.S. patent application entitled "ORTHODONTIC APPLIANCE WITH SELF-RELEASING LATCH", U.S. Ser. No. 09/848,030, which is expressly incorporated by reference herein.

The appliance 10a also includes a retaining guide 30a that extends outwardly from an occlusal side 16a of the body 14a. Optionally, the retaining guide 30a has the configuration shown in FIGS. 6 and 7, with an outer edge segment that is narrower in width in a mesial-distal direction than the mesial-distal width of the retaining guide 30a in areas directly adjacent the occlusal side 16a. In addition, the outer edge of the retaining guide 30a is generally straight and extends in a direction somewhat parallel to the longitudinal axis of the passageway 28a. As another option, the retaining guide 30a may have a configuration of the retaining guide 30 described above and illustrated in FIGS. 1–4.

The appliance 10a also includes two tiewings 76a that are connected to a gingival side 20a of the body 14a. The mesial tiewing 76a is integrally connected to a hook 78a. The tiewings 76a are similar to tiewings of conventional brackets known in the art. The tiewings 76a are useful, for example, in initial stages of treatment in instances where the appliance 10a is located a substantial distance from the archwire as might occur when the tooth is severely maloccluded. In those instances, the tiewings 76a together with the retaining guide 30a can be used together with a ligature for establishing a connection between the appliance 10a and the archwire.

The guides 30, 30a as described above can also be advantageously used to retain items other than tieback loops for closing spaces between adjacent teeth. For example, the guides 30, 30a may be used to hold in captive relationship a wire segment that secures a number of teeth together, as may be needed to serve as anchorage for another orthodontic appliance. The guides 30, 30a may also serve to retain other certain elongated members in place along the sides of the body that are connected to other teeth or serve as a point of connection for other devices used during the course of orthodontic treatment.

The examples described above are intended to exemplify the various aspects and benefits of the invention. However, those skilled in the art may recognize that a number of variations and additions to the appliances described above may be made without departing from the spirit of the invention. Accordingly, the invention should not be deemed limited to the specific embodiments set out above in detail, but instead only by a fair scope of the claims that follow along with their equivalents.

What is claimed is:

1. An orthodontic appliance comprising:
   a base;
   a body extending outwardly from the base, the body having an occlusal side, a labial side and a gingival side;
   an elongated archwire passageway for receiving an archwire; and
   a retaining guide extending outwardly from the body and connected to one of the occlusal side and the gingival side of the body, wherein the guide has an overall generally triangular configuration when viewed in a direction toward the body along a generally occlusal-gingival reference axis.

2. An orthodontic appliance according to claim 1 wherein the guide has an outer edge section remote from the body, wherein the guide extends in a mesial-distal direction a certain distance, and wherein the certain distance increases in size as the outer edge section is approached.

3. An orthodontic appliance according to claim 2 wherein the certain distance steadily increases in size as the outer edge section is approached.

4. An orthodontic appliance according to claim 2 wherein the guide presents a smoothly curved outer surface when viewed in directions toward the base along a labial-lingual reference axis.

5. An orthodontic appliance according to claim 2 wherein the guide is connected to the occlusal side of the body, wherein the occlusal side generally extends in a reference plane that is parallel to the longitudinal axis of the passageway, wherein the guide has an outer edge when viewed in a lingual direction, wherein a straight line drawn tangent to a steepest portion of the outer edge does not exceed an angle of 45 degrees with respect to the reference plane.

6. An orthodontic appliance according to claim 1 wherein the guide has a lingual side for contact with a wire or elastic member, wherein the lingual side extends in a curve about a reference axis that is generally parallel to the longitudinal axis of the passageway, and wherein the curve extends less than about 180 degrees about the reference axis.

7. An orthodontic appliance according to claim 1 wherein the appliance is an orthodontic bracket.

8. An orthodontic appliance according to claim 1 wherein the guide has an outer edge in an occlusal-gingival direction from the one of the occlusal side and the ginival side extending no more than about 0.020.

9. An orthodontic appliance according to claim 1 wherein the guide presents an overall domed appearance when viewed in directions toward the base along a labial-lingual reference axis.

10. An orthodontic appliance according to claim 1 wherein the guide has an outer edge section remote from the body, wherein the guide extends in a mesial-distal direction a certain distance, and wherein the certain distance is largest along the outer edge section.

11. An orthodontic appliance according to claim 1 wherein the appliance is a buccal tube appliance.

12. An orthodontic appliance according to claim 1 wherein the appliance is a self-ligating bracket.

13. An orthodontic appliance according to claim 1 wherein the passageway is enclosed along occlusal, labial, gingival and lingual sides.

14. An orthodontic appliance according to claim 1 wherein the passageway is a slot having an open labial side.

15. An orthodontic appliance comprising:
   a base;
   a body extending outwardly from the base, the body having an occlusal side, a labial side and a gingival side;
   an elongated archwire passageway for receiving an archwire; and
   a guide extending away from the body for retaining a wire segment or other item in place, the guide being connected to a certain one of the occlusal side and the gingival side of the body, and having an outer edge the guide has an overall dome-shaped configuration and an outer edge when viewed in a lingual direction, wherein a straight line drawn tangent to a steepest portion of the outer edge does not exceed an angle of about 45 degrees with respect to a reference plane of the certain side.

16. An orthodontic appliance according claim 15 wherein the outer edge extends in an occlusal-gingival direction from the certain side no more than about 0.020 in.

17. An orthodontic appliance according to claim 15 wherein the guide has an outer edge section remote from the body, wherein the guide extends in a mesial-distal direction a certain distance, and wherein the certain distance increases in size as the outer edge section is approached.

18. An orthodontic appliance according to claim 17 wherein the guide presents a generally triangular shape when viewed in a direction toward the body along an occlusal-gingival reference axis.

19. An orthodontic appliance according to claim 18 wherein the guide presents a domed appearance when viewed in directions toward the base along a labial-lingual reference axis.

20. An orthodontic appliance according to claim 15 wherein the guide has an outer edge section remote from the body, wherein the guide extends in a mesial-distal direction a certain distance, and wherein the certain distance is largest along the outer edge section.

21. An orthodontic appliance according to claim 15 wherein the appliance is a buccal tube appliance.

22. An orthodontic appliance according to claim 15 wherein the appliance is a self-ligating bracket.

23. An orthodontic appliance according to claim 15 wherein the passageway is enclosed along occlusal, labial, gingival and lingual sides.

24. An orthodontic appliance according to claim 15 wherein the passageway is a slot having an open labial side.

* * * * *

UNITED STATES PATENT AND TRADEMARK OFFICE
CERTIFICATE OF CORRECTION

PATENT NO. : 6,709,268 B2
DATED : March 23, 2004
INVENTOR(S) : Pospisil, Jirina V.

It is certified that error appears in the above-identified patent and that said Letters Patent is hereby corrected as shown below:

Title Page
Item [56], References Cited, U.S. PATENT DOCUMENTS, delete "2001/0029008" and insert -- 2002/002900801 --, therefor.

Column 7
Line 22, Delete "arecrooked" and insert -- are crooked --, therefor.

Column 1,
Lines 61-63, after "edge" delete "in an occlusal-gingival direction from the one of the occlusal side and the ginival side extending no more than about 0.020" and insert -- extending no more than about 0.020 in. in an occlusalgingival direction from the one of the occlusal side and the gingival side --, therefor.

Column 11
Line 26, after "body," delete "and having an outer edge".

Column 12
Lines 2-3, after "extends" delete "in an occlusal-gingival direction from the certain side no more than about 0.020 in" and insert -- no more than about 0.020 in. in an occlusal-gingival direction from the certain side --, therefor.
Line 13, delete "claim 18" and insert -- claim 17 --, therefor.

Signed and Sealed this

Twenty-fifth Day of May, 2004

JON W. DUDAS
*Acting Director of the United States Patent and Trademark Office*